United States Patent
Jang et al.

(10) Patent No.: US 9,809,608 B2
(45) Date of Patent: Nov. 7, 2017

(54) CYCLODISILAZANE DERIVATIVE, METHOD FOR PREPARING THE SAME AND SILICON-CONTAINING THIN FILM USING THE SAME

(71) Applicant: DNF CO., LTD., Daejeon (KR)

(72) Inventors: Se Jin Jang, Daegu (KR); Byeong-il Yang, Daejeon (KR); Sung Gi Kim, Daejeon (KR); Jong Hyun Kim, Daejeon (KR); Do Yeon Kim, Gyeongsangbuk-do (KR); Sang-Do Lee, Daejeon (KR); Jang Hyeon Seok, Daejeon (KR); Sang Ick Lee, Daejeon (KR); Myong Woon Kim, Daejeon (KR)

(73) Assignee: DNF CO., LTD., Daejeon (KR)

( * ) Notice: Subject to any disclaimer, the term of this patent is extended or adjusted under 35 U.S.C. 154(b) by 0 days.

(21) Appl. No.: 15/110,707

(22) PCT Filed: Jan. 8, 2015

(86) PCT No.: PCT/KR2015/000189
§ 371 (c)(1),
(2) Date: Jul. 8, 2016

(87) PCT Pub. No.: WO2015/105350
PCT Pub. Date: Jul. 16, 2015

(65) Prior Publication Data
US 2016/0326193 A1 Nov. 10, 2016

(30) Foreign Application Priority Data
Jan. 8, 2014 (KR) .................. 10-2014-0002202

(51) Int. Cl.
*C07F 7/00* (2006.01)
*C07F 7/21* (2006.01)
*H01L 21/02* (2006.01)
*C23C 16/40* (2006.01)
*C23C 16/455* (2006.01)

(52) U.S. Cl.
CPC .............. *C07F 7/21* (2013.01); *C23C 16/402* (2013.01); *C23C 16/45553* (2013.01); *H01L 21/0217* (2013.01); *H01L 21/0228* (2013.01); *H01L 21/02164* (2013.01); *H01L 21/02222* (2013.01); *H01L 21/02274* (2013.01)

(58) Field of Classification Search
CPC ............. C07F 7/21; C23C 16/04; H01L 21/02
USPC ......................................................... 556/409
See application file for complete search history.

(56) References Cited

U.S. PATENT DOCUMENTS

| 4,950,950 A | 8/1990 | Perry et al. |
|---|---|---|
| 2004/0096582 A1 | 5/2004 | Wang et al. |
| 2005/0163927 A1 | 7/2005 | McSwiney et al. |
| 2006/0228903 A1 | 10/2006 | McSwiney et al. |

FOREIGN PATENT DOCUMENTS

| EP | 2048700 A2 | 4/2009 |
|---|---|---|
| KR | 1020070055898 A | 5/2007 |
| WO | 9217527 A1 | 10/1992 |
| WO | 2004044958 A2 | 5/2004 |
| WO | 2013058061 A1 | 4/2013 |

OTHER PUBLICATIONS

Breed et al., Inorg. Chem. 1972 1634-1638.*
Silaghi-Dumitrescu, et al., Journal of Molecular Structure (Theochem) 397 (1997) 213-222.*
Silaghi-Dumitrescu, I. et al., On the formation of cyclodisdilazanes via the coordination of bis(dialkylaminosilanes) to halogenosilanes: an ab initio and AM1 molecular orbital study of the 4644 R2Si(NR'2)2 : SiX4 ring systems, Journal of Molecular Structure (Theochem), vol. 397, No. 1-3, May 1997, 11 pages.
Rayez, M. et al., "Structures and Si—N bond strengths of some cyclodi- and cyclotrisilazanes," Journal of Molecular Structure (Theochem), Vol 487, No. 3, Sep. 23, 1999, 11 pages.
ISA Korean Intellectual Property Office, International Search Report Issued in Application No. PCT/KR2015/000189, dated Apr. 8, 2015, WIPO, 3 pages.
Jaschke, B. et al., "1,3-Bis(silyl)cyclodisilazane: synthesis and crystal structure," Journal of the Chemical Society, Dalton Transactions, No. 18, Jan. 1, 1998, 2 pages.

* cited by examiner

*Primary Examiner* — Sudhakar Katakam
*Assistant Examiner* — Kofi Adzamli
(74) *Attorney, Agent, or Firm* — McCoy Russell LLP

(57) ABSTRACT

Provided are a novel cyclodisilazane derivative, a method for preparing the same, and a silicon-containing thin film using the same, wherein the cyclodisilazane derivative having thermal stability, high volatility, and high reactivity and being present in a liquid state at room temperature and under a pressure where handling is easy, may form a high purity silicon-containing thin film having excellent physical and electrical properties by various deposition methods.

12 Claims, 8 Drawing Sheets

FIG. 6

| Precursor | Thickness (Å) | | | Step Coverage (%) | |
|---|---|---|---|---|---|
| | Top | Middle | Bottom | Side | Bottom |
| 1,3-di-isopropyl-2,4-dimethylcyclodisilazane | 317 | 316 | 323 | 99.68 | 101.89 |
| 1,3-di-isopropyl-4,4-dimethylcyclodisilazane | 436 | 437 | 428 | 100.23 | 98.17 |

CYCLODISILAZANE DERIVATIVE, METHOD FOR PREPARING THE SAME AND SILICON-CONTAINING THIN FILM USING THE SAME

CROSS REFERENCE TO RELATED APPLICATIONS

The present application is a U.S. National Phase of International Patent Application Serial No. PCT/KR2015/000189, entitled "NOVEL CYCLODISILAZANE DERIVATIVE, METHOD FOR PREPARING THE SAME AND SILICON-CONTAINING THIN FILM USING THE SAME," filed on Jan. 8, 2015, which claims priority to Korean Patent Application No. 10-2014-0002202, entitled "NOVEL CYCLODISILAZANE DERIVATIVE, METHOD FOR PREPARING THE SAME AND SILICON-CONTAINING THIN FILM USING THE SAME," filed on Jan. 8, 2014, the entire contents of each of which are hereby incorporated by reference for all purposes.

TECHNICAL FIELD

The present invention relates to a novel cyclodisilazane derivative, a method for preparing the same, and a silicon-containing thin film using the same, and more particularly, to a novel cyclodisilazane derivative having thermal stability and high volatility and being present in a liquid state at room temperature and under a pressure where handling is easy, a method for preparing the same, and a silicon-containing thin film using the same.

BACKGROUND ART

A silicon-containing thin film is manufactured in various shapes, such as a silicon film, a silicon oxide film, a silicon nitride film, a silicon carbonitride film, a silicon oxynitride film, and the like, by various deposition processes in a semiconductor field, and is variously applied to many fields.

In particular, the silicon oxide film and the silicon nitride film may function as an insulating film, a diffusion prevention film, a hard mask, an etching stop layer, a seed layer, a spacer, trench isolation, intermetallic dielectric material and a protective layer in manufacturing a device, due to significantly excellent block property and oxidation resistance.

Recently, polycrystalline silicon thin film has been used for a thin film transistor (TFT), a solar cell, and the like, and therefore, the application field thereof has varied.

As a representative technology known for manufacturing a silicon-containing thin film, there are metal organic chemical vapor deposition (MOCVD) forming a film on a surface of a substrate by reacting a silicon precursor in a mixed gas form and a reactive gas, or forming a film by direct reaction on a surface, and atomic layer deposition (ALD) forming a film by physical or chemical adsorption of a silicon precursor in a gas form on a surface of a substrate, followed by sequential introduction of a reactive gas. In addition, various technologies for manufacturing a thin film such as low pressure chemical vapor deposition (LPCVD), plasma enhanced chemical vapor deposition (PECVD), plasma enhanced atomic layer deposition (PEALD) using plasma capable of being deposited at a low temperature, and the like, are applied to a next-generation semiconductor and a display device manufacturing process, thereby being used to form ultra-fine patterns and deposit ultra-thin film having uniform and excellent properties at a nano-sized thickness.

Representative examples of a precursor used in forming a silicon-containing thin film as described in Korean Patent Laid-Open Publication No. KR 2007-0055898 include silanes, silane chlorides, amino silanes and alkoxysilanes, and more specifically, silane chlorides such as dichlorosilane ($SiH_2Cl_2$) and hexachlorodisilane ($Cl_3SiSiCl_3$) and trisilylamine ($N(SiH_3)_3$), bis-diethylaminosilane ($H_2Si(N(CH_2CH_3)_2)_2$) and di-isopropylaminosilane ($H_3SiN(i-C_3H_7)_2$), and the like, and used in a mass production of a semiconductor and a display.

However, a technology of forming an ultra-fine thin film having a uniform and thin thickness and excellent electrical properties at a desired low temperature according to miniaturization of devices caused by ultra-high integration of the devices, an increase in an aspect ratio, and diversification of device material has been demanded, and thus, high temperature process at 600° C. or more, step coverage, etching property, and physical and electrical properties of a thin film at the time of using the existing silicon precursor are emerging as an issue, and accordingly, excellent novel silicon precursor has been demanded to be developed.

RELATED ART DOCUMENT (Patent Document 1) Korean Patent Laid-Open Publication No. KR 2007-0055898
(Patent Document 2) U.S. Patent Application Publication No. 2004-0096582A1

DISCLOSURE

Technical Problem

An object of the present invention is to provide a cyclodisilazane derivative.

In addition, another object of the present invention is to provide a novel cyclodisilazane derivative which is a precursor compound for thin film deposition.

Further, another object of the present invention is to provide a method for preparing a cyclodisilazane derivative.

In addition, another object of the present invention is to provide a composition for depositing a silicon-containing thin film, which includes the cyclodisilazane derivative of the present invention, a method for manufacturing a silicon-containing thin film by using the cyclodisilazane derivative of the present invention, and the silicon-containing thin film manufactured by including the cyclodisilazane derivative of the present invention.

Technical Solution

In one general aspect, the present invention provides a novel cyclodisilazane derivative capable of forming a silicon thin film having excellent cohesion, high deposition rate, and excellent physical and electrical properties even at a low temperature.

The novel cyclodisilazane derivative of the present invention is represented by the following Chemical Formula 1:

[Chemical Formula 1]

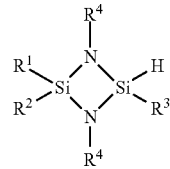

in Chemical Formula 1, $R^1$ to $R^3$ are each independently hydrogen, halogen, (C1-C5)alkyl or (C2-C5)alkenyl, and $R^4$ is hydrogen, (C1-C3)alkyl or (C2-C5)alkenyl.

The cyclodisilazane derivative of the present invention is a liquid-state compound at room temperature and under atmospheric pressure to have superior volatility, thereby allowing a thin film to be easily formed. In addition, the cyclodisilazane derivative, which is a stable square-shaped ring compound having a Si—N bond, has an advantage of controlling symmetry and asymmetry of a compound according to a substituent group to be capable of controlling reactivity. Further, due to the molecular structure having the square-shaped ring, the cyclodisilazane derivative of the present invention has high thermal stability and low activation energy to thereby have excellent reactivity, and does not generate non-volatile by-product to be capable of easily forming a silicon-containing thin film having high purity.

In order for the cyclodisilazane derivative represented by Chemical Formula 1 according to an exemplary embodiment of the present invention to form a thin film having high thermal stability and reactivity, and high purity, it is preferred that in Chemical Formula 1, $R^1$ to $R^3$ are each independently hydrogen, halogen, (C1-C3)alkyl or (C2-C3)alkenyl, and $R^4$ is (C1-C3)alkyl or (C2-C3)alkenyl, and it is more preferred that in Chemical Formula 1, $R^1$ to $R^3$ are each independently hydrogen, halogen, methyl or ethenyl, and $R^4$ is isopropyl or isopropenyl.

The cyclodisilazane derivative represented by Chemical Formula 1 according to an exemplary embodiment of the present invention may be selected from the following compounds, but the present invention is not limited thereto:

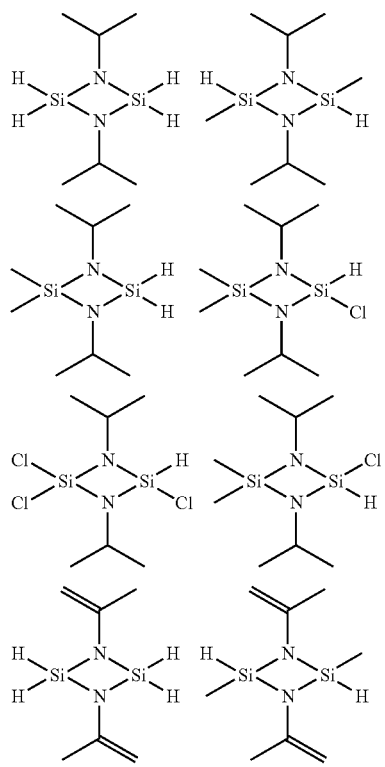

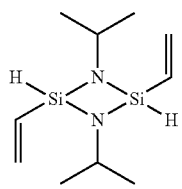

Terms: [alkyl] described in the present invention includes both of linear type or branched type.

In addition, the cyclodisilazane derivative represented by Chemical Formula 1 of the present invention may be preferably a precursor compound for depositing a silicon-containing thin film.

Further, in another general aspect, the present invention provides a method for preparing a cyclodisilazane derivative represented by the following Chemical Formula 1.

The method for preparing the cyclodisilazane derivative of the present invention includes preparing a diaminosilane derivative represented by the following Chemical Formula 4 by reacting a silane derivative represented by the following Chemical Formula 2 with an amine derivative represented by the following Chemical Formula 3; and preparing the cyclodisilazane derivative represented by the following Chemical Formula 1 by an intramolecular cyclization reaction of the diaminosilane derivative represented by the following Chemical Formula 4 with a silane derivative represented by the following Chemical Formula 5 in the presence of (C1-C7)alkyllithium:

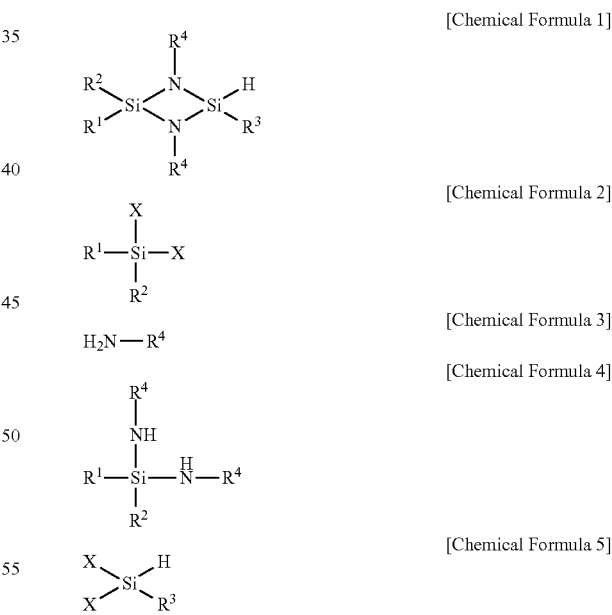

in Chemical Formulas 1 to 5, $R^1$ to $R^3$ are each independently hydrogen, halogen, (C1-C5)alkyl or (C2-C5)alkenyl, $R^4$ is hydrogen, (C1-C3)alkyl or (C2-C5)alkenyl, and X is halogen.

In an exemplary embodiment of the present invention, the preparing of the diaminosilane derivative represented by Chemical Formula 4 may be performed in the presence of a base represented by the following Chemical Formula 10 or (C1-C7)alkyllithium:

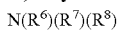  [Chemical Formula 10]

in Chemical Formula 10, $R^6$ to $R^8$ are each independently (C1-C7)alkyl.

In another general aspect, the present invention provides a method for preparing a cyclodisilazane derivative represented by the following Chemical Formula 1-2, the method including: preparing the cyclodisilazane derivative represented by the following Chemical Formula 1-2 by reacting a halocyclodisilazane derivative represented by the following Chemical Formula 1-1 with a metal hydride or an alkali metal derivative represented by the following Chemical Formula 8:

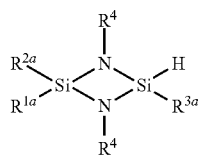  [Chemical Formula 1-2]

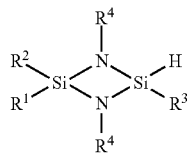  [Chemical Formula 1-1]

  [Chemical Formula 8]

in Chemical Formulas 1-1, 1-2, and 8,
M is an alkali metal;
$R^{10}$ is each independently hydrogen or (C1-C5)alkyl;
at least one of $R^1$ to $R^3$ is halogen, and the remainder is hydrogen, halogen, (C1-C5)alkyl or (C2-C5)alkenyl;
$R^4$ is hydrogen, (C1-C3)alkyl or (C2-C5)alkenyl; and
at least one of $R^{1a}$ to $R^{3a}$ is hydrogen, and the remainder is hydrogen, (C1-C5)alkyl or (C2-C5)alkenyl, wherein when $R^1$ is halogen, $R^{1a}$ is hydrogen, and when $R^2$ is halogen, $R^{2a}$ is hydrogen, and when $R^3$ is halogen, $R^{3a}$ is hydrogen.

In another general aspect, the present invention provides a method for preparing a cyclodisilazane derivative represented by the following Chemical Formula 9, the method including: preparing an aminosilane derivative represented by the following Chemical Formula 6 by reacting a silane derivative represented by the following Chemical Formula 2 with an amine derivative represented by the following Chemical Formula 3; preparing a halocyclodisilazane derivative represented by the following Chemical Formula 7 by an intramolecular cyclization reaction of the aminosilane derivative represented by the following Chemical Formula 6 in the presence of (C1-C7)alkyllithium; and preparing the cyclodisilazane derivative represented by the following Chemical Formula 9 by reacting the halocyclodisilazane derivative represented by the following Chemical Formula 7 with a metal hydride or an alkali metal derivative represented by the following Chemical Formula 8:

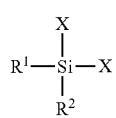  [Chemical Formula 2]

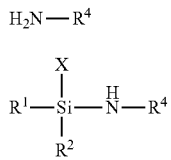  [Chemical Formula 3]

[Chemical Formula 6]

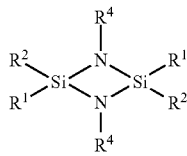  [Chemical Formula 7]

  [Chemical Formula 8]

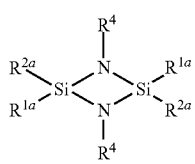  [Chemical Formula 9]

in Chemical Formulas 2, 3 and 6 to 9,
$R^1$ is halogen;
$R^2$ is hydrogen, halogen, (C1-C5)alkyl or (C2-C5)alkenyl;
$R^4$ is hydrogen, (C1-C3)alkyl or (C2-C5)alkenyl;
X is halogen;
M is an alkali metal;
$R^{10}$ is hydrogen or (C1-C5)alkyl;
$R^{1a}$ is hydrogen;
wherein when $R^2$ is hydrogen or halogen, $R^{2a}$ is hydrogen, and
when $R^2$ is (C1-C5)alkyl or (C2-C5)alkenyl, $R^{2a}$ is (C1-C5)alkyl or (C2-C5)alkenyl.

In an exemplary embodiment of the present invention, the preparing of the aminosilane derivative represented by Chemical Formula 6 may be performed in the presence of a base represented by the following Chemical Formula 10 or (C1-C7)alkyllithium:

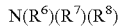  [Chemical Formula 10]

in Chemical Formula 10, $R^6$ to $R^8$ are each independently (C1-C7)alkyl.

(C1-C7)alkyllithium according to an exemplary embodiment of the present invention is a compound where lithium is bonded to (C1-C7)alkyl, for example, methyllithium, n-butyllithium, and the like, and preferably, n-butyllithium.

The metal hydride according to an exemplary embodiment of the present invention may be one or a mixture of two or more, selected from the group consisting of LiH, NaH, KH and LiAlH$_4$.

Solvents used in the preparation method of the present invention are not limited if they are not reacted with the starting material among general organic solvents, for example, may be at least one selected from the group consisting of normalhexane (n-hexane), cyclohexane, normalpentane (n-pentane), diethyl ether, toluene, tetrahydrofuran (THF), dichloromethane (DCM), and trichloromethane (chloroform).

A reaction temperature in the preparation method of the present invention is not limited if a temperature is used for general organic synthesis; however, may be varied depending on an amount of the reaction time, the reaction material, and the starting material, wherein the reaction needs to be finished after confirming that the starting material is completely consumed by NMR, GC, and the like. When the reaction is finished, the solvent may be removed by filtration, followed by simple distillation under reduced pressure, and then a desired material may be separated and refined by general methods such as fractional distillation, distillation under reduced pressure, and the like.

In another general aspect, the present invention provides a composition for depositing a silicon-containing thin film, including the cyclodisilazane derivative as described above.

The composition for depositing the silicon-containing thin film of the present invention may contain the cyclodisilazane derivative of the present invention as a precursor for thin film deposition, and the cyclodisilazane derivative in the composition may have a content within the range which is recognizable by a person skilled in the art in consideration of film forming conditions, or thickness, properties, and the like, of the thin film.

In another general aspect, the present invention provides a method for manufacturing a silicon-containing thin film by using the cyclodisilazane derivative as described above.

In another general aspect, the present invention provides a silicon-containing thin film manufactured by including the cyclodisilazane derivative as described above.

The silicon-containing thin film of the present invention may be manufactured by general methods, for example, metal organic chemical vapor deposition (MOCVD), atomic layer deposition (ALD), low pressure chemical vapor deposition (LPCVD), plasma enhanced chemical vapor deposition (PECVD), plasma enhanced atomic layer deposition (PEALD), and the like.

The cyclodisilazane derivative of the present invention has low activation energy and high reactivity, and minimizes generation of non-volatile by-product, such that the silicon-containing thin film manufactured by using the cyclodisilazane derivative as a precursor may have high purity and excellent physical and electrical properties.

Advantageous Effects

The cyclodisilazane derivative of the present invention has excellent thermal stability and high reactivity, such that the silicon-containing thin film manufactured by using the cyclodisilazane derivative as a precursor may have high purity and significantly excellent physical and electrical properties.

In addition, the cyclodisilazane derivative of the present invention may have high content of silicon and is present in a liquid state at room temperature and under atmospheric pressure to thereby be easily stored and handled, and may have high volatility and high reactivity to be rapidly and easily deposited, and it is possible to deposit a thin film having excellent cohesion and superior step coverage.

DESCRIPTION OF DRAWINGS

The above and other objects, features and advantages of the present invention will become apparent from the following description of preferred embodiments given in conjunction with the accompanying drawings, in which:

FIG. 6 shows results obtained by a step coverage analysis of the silicon-containing thin films practiced by Example 7, using Transmission Electron Microscopy.

BEST MODE

Figure 1:
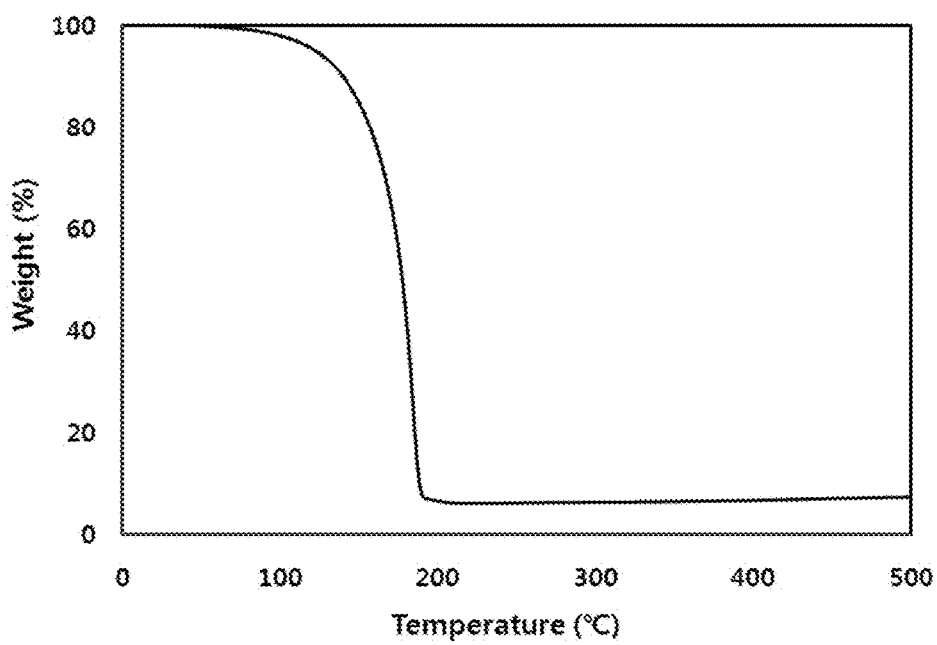
FIG. 1 shows a result obtained by thermogravimetric analysis of 1,3-diisopropyl-2,4-dimethylcyclodisilazane prepared by Example 1.
Figure 2:
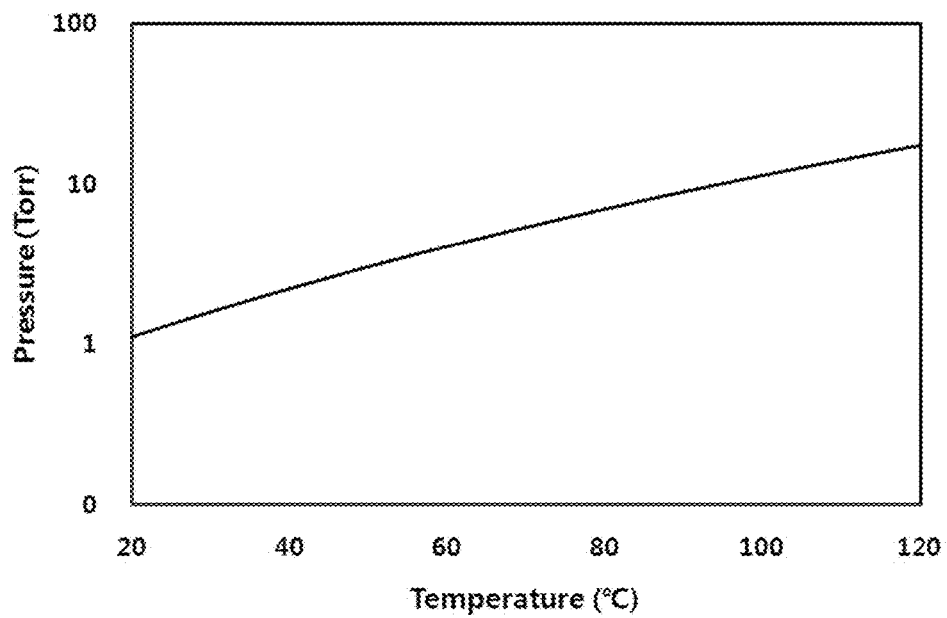
FIG. 2 shows a result obtained by vapor pressure measurement of 1,3-diisopropyl-2,4-dimethylcyclodisilazane prepared by Example 1.
Figure 3:
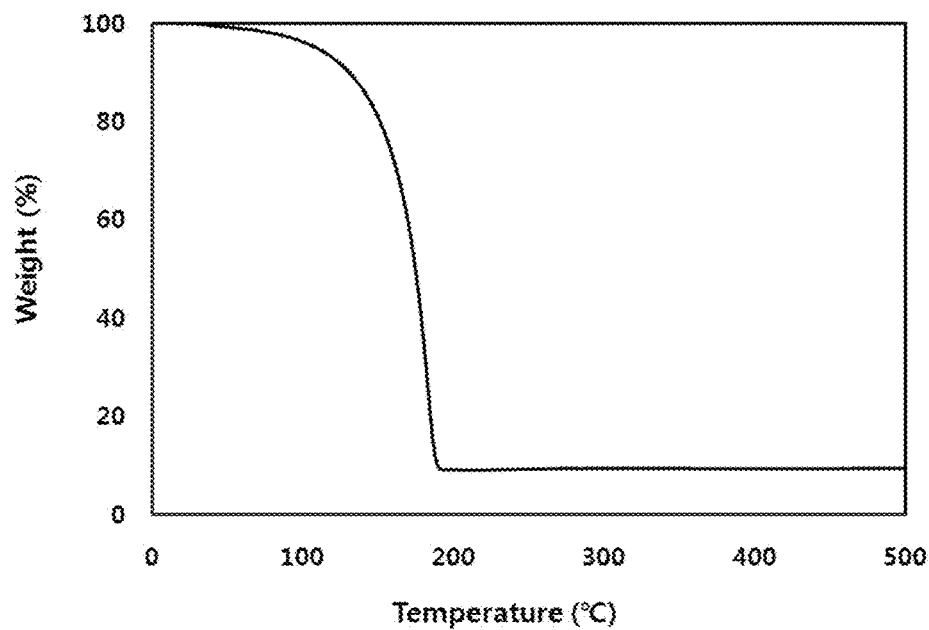
FIG. 3 shows a result obtained by thermogravimetric analysis of 1,3-diisopropyl-4,4-dimethylcyclodisilazane prepared by Example 6.
Figure 4:
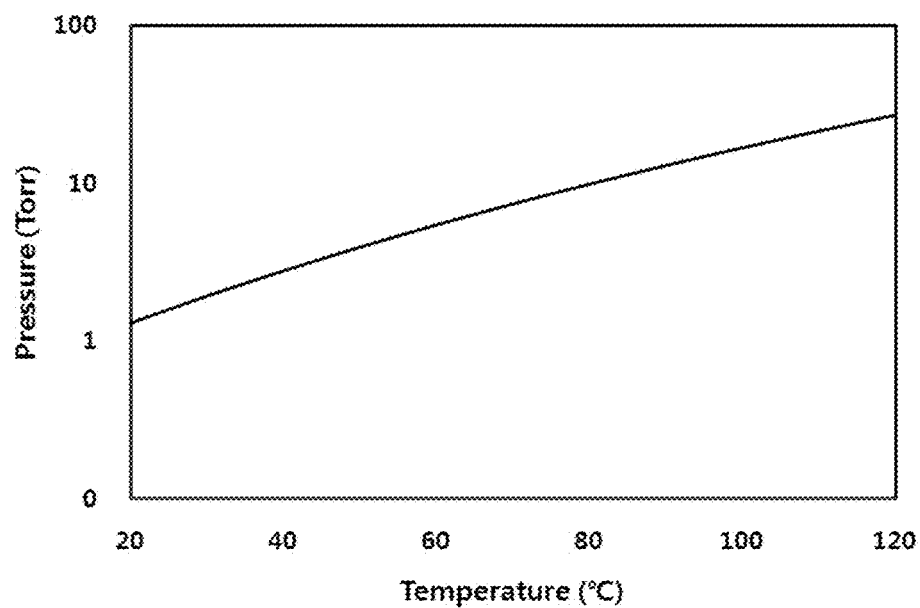
FIG. 4 shows a result obtained by vapor pressure measurement of 1,3-diisopropyl-4,4-dimethylcyclodisilazane prepared by Example 6.

Hereinafter, the present invention will be described in more detail with reference to the following exemplary embodiments. However, the following exemplary embodiments describe the present invention by way of example only but are not limited thereto.

The following Examples of all compounds were practiced under anhydrous and inert atmosphere using a glovebox or a Schlenk pipe, products were analyzed by $^1$H Nuclear Magnetic Resonance (NMR, 400 MHz Ultrashield, Buruker), thermogravimetric analysis (TGA, L81-II, LINSEIS) and gas chromatography (GC, 7890A, Agilent Technologies), thickness of deposited thin films were measured by an Ellipsometer (M2000D, Woollam), and components of the films were analyzed by infrared spectroscopy (IFS66V/S & Hyperion 3000, Bruker Optiks) and auger electron spectroscopy (Microlab 350, Thermo Electron).

EXAMPLE 1

Synthesis of
1,3-diisopropyl-2,4-dimethylcyclodisilazane

1) Synthesis of 1,3-diisopropyl-2,4-dichlorodimethylcyclodisilazane 127 g (0.86 mol) of trichloro(methyl)silane ($CH_3SiCl_3$) and 1200 ml of an organic solvent (n-hexane) were put into a 2000 mL flame-dried Schlenk flask and stirred under anhydrous and inert atmosphere, and 101.7 g (1.72 mol) of isopropylamine ($H_2NCH(CH_3)_2$) was slowly added thereto while maintaining temperature at −10° C. After the addition was completed, a temperature of the reaction solution was slowly raised to room temperature, and the reaction solution was stirred at room temperature for 3 hours. After the stirring was completed, the reaction solution was filtrated, and a white solid obtained by the filtration was removed to obtain a filtrate. 200 ml of an organic solvent (n-hexane) was put into dichloro(methyl)(isopropylamino)silane ($Cl_2CH_3SiNHCH(CH_3)_2$) recovered after the solvent was removed from the filtrate under reduced pressure, and stirred, and then 367.0 g (0.90 mol) of 1.7M t-butyllithium (t-$C_4H_9Li$) hexane ($C_6H_{14}$) solution was slowly added thereto while maintaining temperature at 40° C. After the addition was completed, a temperature of the reaction solution was slowly raised to 65° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 81.4 g (0.30 mol) of 1,3-diisopropyl-2,4-dichlorodimethylcyclodisilazane (($ClCH_3SiNCH(CH_3)_2)_2$) was obtained by reduced pressure distillation with a yield of 70%.

$^1$H NMR (in $C_6D_6$) δ 0.50, 0.53(s, 6H, csi-NSi($CH_3$)Cl, trans-NSi($CH_3$)Cl), 1.07(d, 12H, Si(NCH($CH_3$)$_2$), 3.27(m, 2H, Si(NCH($CH_3$)$_2$); Boiling Point 197° C.

2) Synthesis of 1,3-diisopropyl-2,4-dimethylcyclodisilazane 100 g (0.37 mol) of 1,3-diisopropyl-2,4-dichlorodimethyl cyclodisilazane (($ClCH_3SiNCH(CH_3)_2)_2$) synthesized in the above 1) and 200 ml of an organic solvent (THF) were put into a 1000 mL flame-dried Schlenk flask and stirred under anhydrous and inert atmosphere, and 7.33 g (0.92 mol) of lithium hydride (LiH) was slowly added thereto while maintaining temperature at −15° C. After the addition was completed, a temperature of the reaction solution was slowly raised to 65° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 60 g (0.3 mol) of 1,3-diisopropyl-2,4-dimethylcyclodisilazane (($HCH_3SiNCH(CH_3)_2)_2$) was obtained by reduced pressure distillation with a yield of 80%.

$^1$H NMR (in $C_6D_6$) δ 0.33(m, 6H, NSiH($CH_3$)), 1.05(m, 12H, Si(NCH($CH_3$)$_2$), 3.20(m, 2H, Si(NCH($CH_3$)$_2$), 5.52 (m, 2H, NSiH($CH_3$)); Boiling Point 173~175° C.

EXAMPLE 2

Synthesis of 1,3-diisopropyl cyclodisilazane

1) Synthesis of 1,3-diisopropyl-2,2,4,4-tetrachlorocyclodisilazane 150 g (0.89 mol) of tetrachlorosilane ($SiCl_4$) and 500 ml of an organic solvent (n-hexane) were put into a 2000 mL flame-dried Schlenk flask and stirred under anhydrous and inert atmosphere, and 104.76 g (1.77 mol) of isopropylamine ($H_2NCH(CH_3)_2$) was slowly added thereto while maintaining temperature at −10° C. After the addition was completed, a temperature of the reaction solution was slowly raised to room temperature, and the reaction solution was stirred at room temperature for 3 hours. After the stirring was completed, the reaction solution was filtrated, and a white solid obtained by the filtration was removed to obtain a filtrate. 200 ml of an organic solvent (n-hexane) was put into trichloro(isopropylamino)silane ($Cl_3SiNHCH(CH_3)_2$) recovered after the solvent was removed from the filtrate under reduced pressure, and stirred, and then 368.38 g (0.90 mol) of 1.7M t-butyllithium (t-$C_4H_9Li$) hexane ($C_6H_{14}$) solution was slowly added thereto while maintaining temperature at 40° C. After the addition was completed, a temperature of the reaction solution was slowly raised to 65° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 121.7 g (0.35 mol) of 1,3-diisopropyl-2,2,4,4-tetrachlorocyclodisilazane (($Cl_2SiNCH(CH_3)_2)_2$) was obtained by reduced pressure distillation with a yield of 88%.

$^1$H NMR (in $C_6D_6$) δ 1.10(d, 12H, Si(NCH($CH_3$)$_2$), 3.34(m, 2H, Si(NCH($CH_3$)$_2$); Boiling Point 216~217° C.

2) Synthesis of 1,3-diisopropyl cyclodisilazane 80 g (0.26 mol) of 1,3-diisopropyl-2,2,4,4-tetrachlorocyclodisilazane (($Cl_2SiNCH(CH_3)_2)_2$) synthesized in the above 1) and 400 ml of an organic solvent (diethylether) were put into a 2000 mL flame-dried Schlenk flask and stirred under anhydrous and inert atmosphere, and 12.35 g (1.55 mol) of lithium aluminum hydride ($LiAlH_4$) was slowly added thereto while maintaining temperature at −15° C. After the addition was completed, a temperature of the reaction solution was slowly raised to 60° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 26.8 g (0.16 mol) of 1,3-diisopropylcyclodisilazane (($H_2SiNCH(CH_3)_2)_2$) was obtained by reduced pressure distillation with a yield of 60%.

$^1$H NMR (in $C_6D_6$) δ 1.11(d, 12H, Si(NCH($CH_3$)$_2$), 3.23(m, 2H, Si(NCH($CH_3$)$_2$), 4.48(s, 2H, NSiH); Boiling Point 155~160° C.

EXAMPLE 3

Synthesis of 1,3-diisopropyl-2-chloro-4,4-dimethyl cyclodisilazane 214 g (1.66 mol) of dichlorodimethylsilane (Si($CH_3$)$_2Cl_2$) and 1000 ml of an organic solvent (n-hexane) were put into a 2000 mL flame-dried Schlenk flask and stirred under anhydrous and inert atmosphere, and 392.1 g (6.63 mol) of isopropylamine ($H_2NCH(CH_3)_2$) was slowly added thereto while maintaining temperature at −10° C. After the addition was completed, a temperature of the reaction solution was slowly raised to room temperature, and the reaction solution was stirred at room temperature for 3 hours. After the stirring was completed, the reaction solution was filtrated, and a white solid obtained by the filtration was removed to obtain a filtrate. 300 ml of an organic solvent (n-hexane) was put into di(isopropylamino)dimethylsilane (($CH_3$)$_2$Si(NHCH($CH_3$)$_2$)$_2$) recovered after the solvent was removed from the filtrate under reduced pressure, and stirred, and then 1005.3 g (3.32 mol) of 2.5M n-butyllithium (n-$C_4H_9Li$) hexane ($C_6H_{14}$) solution was slowly added thereto while maintaining temperature at −15° C. After the addition was completed, a temperature of the reaction solution was slowly raised to 25° C., and the reaction solution was stirred for 12 hours, and then, 224.6 g (1.66 mol) of trichlorosilane ($SiHCl_3$) was slowly added thereto. After the addition was completed, a temperature of the reaction solution was slowly raised to 65° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 255.3 g (1.08 mol) of 1,3-diisopropyl-2-chloro-4,4-dimethylcyclodisilazane ((($CH_3$)$_2$SiNCH($CH_3$)$_2$)(ClSiHNCH($CH_3$)$_2$)) was obtained by reduced pressure distillation with a yield of 65%.

$^1$H NMR (in $C_6D_6$) δ 0.19 and 0.21 (s, 6H, $NSi(CH_3)_2$), 1.03(d, 12H, $Si(NCH(CH_3)_2)$, 3.17(m, 2H, $Si(NCH(CH_3)_2)$, 5.99(s, 1H, NSiHCl); Boiling Point 190° C.

EXAMPLE 4

Synthesis of 1,3-diisopropyl-2-chloro-4,4-dimethyl cyclodisilazane 107 g (0.83 mol) of dichlorodimethylsilane (($CH_3)_2SiCl_2$) and 400 ml of an organic solvent (n-hexane) were put into a 1000 mL flame-dried Schlenk flask and stirred under anhydrous and inert atmosphere, and 167.7 g (1.66 mol) of triethylamine ($C_2H_5)_3N$) was slowly added thereto while maintaining temperature at −10° C., and then 98.0 g (1.65 mol) of isopropylamine ($H_2NCH(CH_3)_2$) was slowly added thereto while maintaining temperature at −10° C. After the addition was completed, a temperature of the reaction solution was slowly raised to room temperature, and the reaction solution was stirred at room temperature for 3 hours. After the stirring was completed, the reaction solution was filtrated, and a white solid obtained by the filtration was removed to obtain a filtrate. 200 ml of an organic solvent (n-hexane) was put into di(isopropylamino)dimethylsilane (($CH_3)_2Si(NHCH(CH_3)_2)_2$) recovered after the solvent was removed from the filtrate under reduced pressure, and stirred, and then 351.8 g (1.16 mol) of 2.5M n-butyllithium (n-$C_4H_9Li$) hexane ($C_6H_{14}$) solution was slowly added thereto while maintaining temperature at −10° C. After the addition was completed, a temperature of the reaction solution was slowly raised to room temperature, and the reaction solution was stirred for 12 hours, and then, 224.6 g (1.66 mol) of trichlorosilane ($SiHCl_3$) was slowly added thereto. After the addition was completed, a temperature of the reaction solution was slowly raised to 65° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 255.3 g (1.08 mol) of 1,3-diisopropyl-2-chloro-4,4-dimethylcyclodisilazane ((($CH_3)_2SiNCH(CH_3)_2)(ClSiHNCH(CH_3)_2))$ was obtained by reduced pressure distillation with a yield of 65%.

$^1$H NMR (in $C_6D_6$) δ 0.19 and 0.21 (s, 6H, $NSi(CH_3)_2$), 1.03(d, 12H, $Si(NCH(CH_3)_2)$, 3.17(m, 2H, $Si(NCH(CH_3)_2)$, 5.99(s, 1H, NSiHCl); Boiling Point 190° C.

EXAMPLE 5

Synthesis of 1,3-diisopropyl-2-chloro-4,4-dimethyl cyclodisilazane 98.0 g (1.65 mol) of isopropylamine ($H_2NCH(CH_3)_2$) and 400 ml of an organic solvent (n-hexane) were put into a 1000 mL flame-dried Schlenk flask and stirred under anhydrous and inert atmosphere, and 500.4 g (1.65 mol) of 2.5M n-butyllithium (n-$C_4H_9Li$) hexane ($C_6H_{14}$) solution was slowly added thereto while maintaining temperature at −10° C. After the addition was completed, a temperature of the reaction solution was slowly raised to room temperature, and the reaction solution was stirred at room temperature for 3 hours, and then 107 g (0.83 mol) of dichlorodimethylsilane (($CH_3)_2SiCl_2$) was slowly added thereto while maintaining temperature at −10° C. After the addition was completed, a temperature of the reaction solution was slowly raised to room temperature, and the reaction solution was stirred at room temperature for 3 hours. After the stirring was completed, the reaction solution was filtrated, and a white solid obtained by the filtration was removed to obtain a filtrate. 200 ml of an organic solvent (n-hexane) was put into di(isopropylamino)dimethylsilane (($CH_3)_2Si(NHCH(CH_3)_2)_2$) recovered after the solvent was removed from the filtrate under reduced pressure, and stirred, and then 351.8 g (1.16 mol) of 2.5M n-butyllithium (n-$C_4H_9Li$) hexane ($C_6H_{14}$) solution was slowly added thereto while maintaining temperature at −10° C. After the addition was completed, a temperature of the reaction solution was slowly raised to room temperature, and the reaction solution was stirred for 12 hours, and then, 224.6 g (1.66 mol) of trichlorosilane ($SiHCl_3$) was slowly added thereto. After the addition was completed, a temperature of the reaction solution was slowly raised to 65° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 196.4 g (0.83 mol) of 1,3-diisopropyl-2-chloro-4,4-dimethylcyclodisilazane ((($CH_3)_2SiNCH(CH_3)_2)(ClSiHNCH(CH_3)_2))$ was obtained by reduced pressure distillation with a yield of 50%.

$^1$H NMR (in $C_6D_6$) δ 0.19 and 0.21 (s, 6H, $NSi(CH_3)_2$), 1.03(d, 12H, $Si(NCH(CH_3)_2)$, 3.17(m, 2H, $Si(NCH(CH_3)_2)$, 5.99(s, 1H, NSiHCl); Boiling Point 190° C.

EXAMPLE 6

Synthesis of 1,3-diisopropyl-4,4-dimethylcyclodisilazane 200 g (0.84 mol) of 1,3-diisopropyl-2-chloro-4,4-dimethylcyclodisilazane ((($CH_3)_2SiNCH(CH_3)_2)(ClSiHNCH(CH_3)_2))$ synthesized in Example 3 above and 600 ml of an organic solvent (THF) were put into a 2000 mL flame-dried Schlenk flask and stirred under anhydrous and inert atmosphere, 7.4 g (0.93 mol) of lithium hydride (LiH) was slowly added thereto while maintaining temperature at −15° C. After the addition was completed, a temperature of the reaction solution was slowly raised to 65° C., and the reaction solution was stirred for 12 hours. After the stirring was completed, the reaction solution was filtrated, and a white solid obtained by the filtration was removed to obtain a filtrate, and then a solvent was removed from the filtrate under reduced pressure, and 85.46 g (0.42 mol) of 1,3-diisopropyl-4,4-dimethylcyclodisilazane ((($CH_3)_2SiNCH(CH_3)_2)(SiH_2NCH(CH_3)_2))$ was obtained by reduced pressure distillation with a yield of 50%.

$^1$H NMR (in $C_6D_6$) δ 0.26(s, 6H, $NSi(CH_3)_2$), 1.06(d, 12H, $Si(NCH(CH_3)_2)$, 3.18(m, 2H, $Si(NCH(CH_3)_2)$, 5.51(s, 1H, $NSiH_2$); Boiling Point 175° C.

EXAMPLE 7

Figure 5:
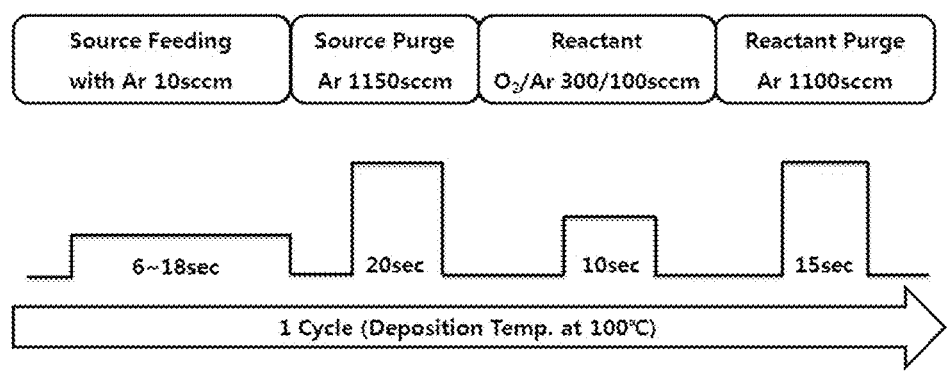
FIG. 5 shows a method for depositing silicon-containing thin films practiced by Example 7 and Comparative Example 1.

Deposition of Silicon Oxide Film by Plasma Enhanced Atomic Layer Deposition (PEALD) Using Cyclodisilazane Derivative Film forming evaluation was conducted by using 1,3-diisopropyl-2,4-dimethylcyclodisilazane of Example 1 and 1,3-diisopropyl-4,4-dimethylcyclodisilazane of Example 6 according to the present invention as a composition for forming a silicon oxide film in a general plasma enhanced atomic layer deposition (PEALD) apparatus using the known PEALD method. Oxygen together with plasma was used as the reaction gas, and argon which is an inert gas was used for purge. Hereinafter, FIG. 5 and Table 1 specifically show a method for depositing a silicon oxide thin film.

TABLE 1

Deposition Condition of Silicon Oxide Thin film

|  |  | Precursor | | | |
| --- | --- | --- | --- | --- | --- |
|  |  | 1,3-diisopropyl-2,4-dimethylcyclodisilazane (Example 1) | | 1,3-diisopropyl-4,4-dimethylcyclodisilazane (Example 6) | |
| Heating Temperature (° C.) of Precursor | | 40 | 40 | 40 | 40 |
| Substrate Temperature (° C.) | | 100 | 100 | 100 | 100 |
| Kind of Substrate | | Si wafer | Si Pattern wafer. Hole Size 200 nm Aspect Ratio: 5 | Si wafer | Si Pattern wafer. Hole Size 200 nm Aspect Ratio: 5 |
| Injection Time (sec) of Precursor | | 6 | 18 | 9 | 18 |
| Purge | Flow Amount (sccm) | 1100 | 1100 | 1100 | 1100 |
|  | Time (sec) | 20 | 60 | 20 | 60 |
| 400 W Oxygen Plasma | Flow Amount (sccm) of Oxygen/Argon | 300/100 | 300/100 | 300/100 | 300/100 |
|  | Time (sec) | 10 | 20 | 10 | 20 |
| Purge | Flow Amount (sccm) | 1100 | 1100 | 1100 | 1100 |
|  | Time (sec) | 15 | 30 | 15 | 30 |
| Frequency of Deposition | Cycle | 50 | 273 | 50 | 406 |

A thickness of the deposited thin film was measured by an Ellipsometer, and formation of SiO$_2$ thin film and components of the thin film were analyzed by infrared spectroscopy and auger electron spectroscopy. In 50 cycles on a Si wafer, a thickness of the thin film of 1,3-diisopropyl-2,4-dimethylcyclodisilazane (Example 1) was 76.98 Å and a thickness of the thin film of 1,3-diisopropyl-4,4-dimethylcyclodisilazane (Example 6) was 78.84 Å. In addition, in 273 cycles on a Si pattern wafer, a thickness of the thin film manufactured by including 1,3-diisopropyl-2,4-dimethylcyclodisilazane (Example 1) was 317 Å, and in 406 cycles on a Si pattern wafer, a thickness of the thin film manufactured by including 1,3-diisopropyl-4,4-dimethylcyclodisilazane (Example 6) was 436 Å. Further, step coverage was 98.17 to 101.89%. Therefore, it is determined that these thin films are capable of being effectively used throughout all silicon oxide thin film application fields requiring a high deposition rate and excellent step coverage (FIG. 6).

Figure 7:
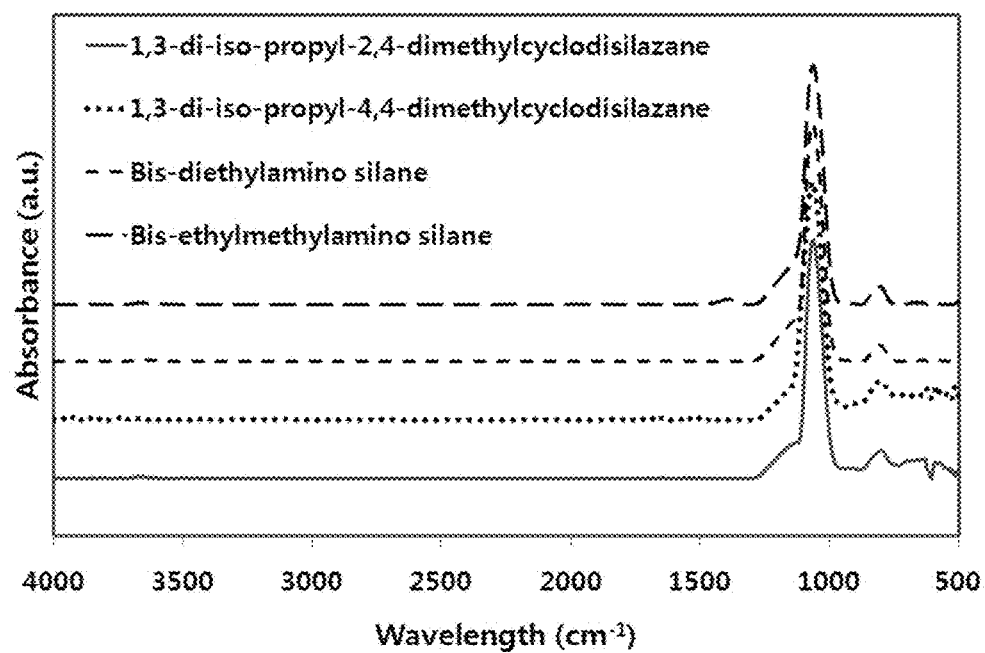
FIG. 7 shows results obtained by an infrared spectroscopic analysis of the silicon-containing thin films practiced by Example 7 and Comparative Example 1.
Figure 8A:
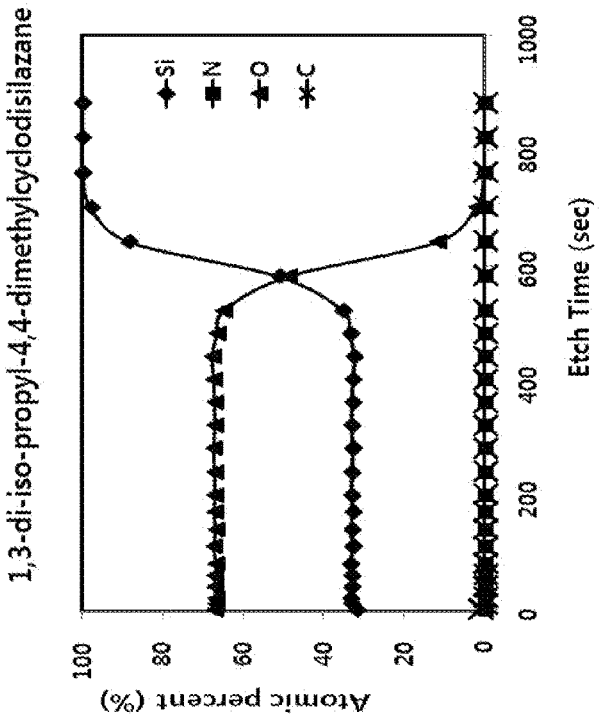
FIGS. 8A and 8B show results obtained by an auger electron spectroscopic analysis of the silicon-containing thin films practiced by Example 7.
Figure 8B:
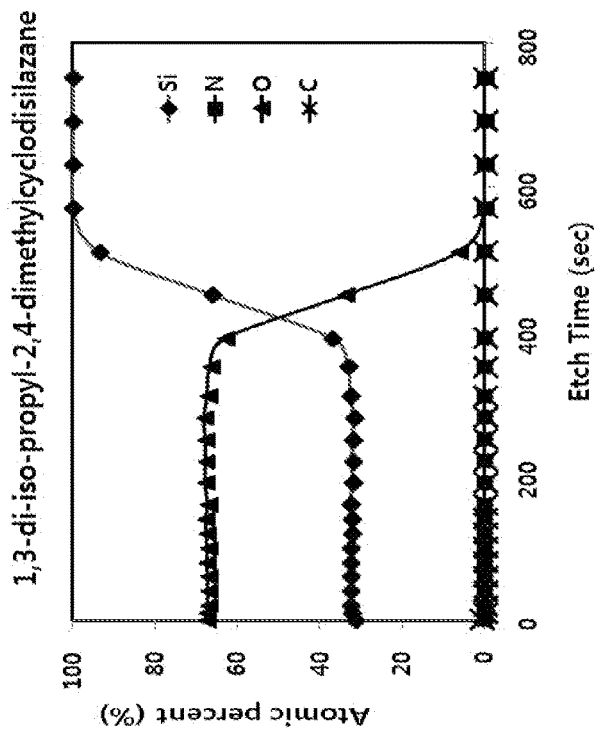

In addition, as shown in FIGS. 7 and 8, all of the deposited thin films were formed as silicon oxide films, and peak of impurities such as C—H, Si—OH was not observed (FIG. 7). A ratio between oxygen and silicon in the thin film formed by using 1,3-diisopropyl-2,4-dimethylcyclodisilazane (Example 1) was 2.07:1 and a ratio between oxygen and silicon in the thin film formed by using 1,3-diisopropyl-4,4-dimethylcyclodisilazane (Example 6) was 2.03:1, and carbon and nitrogen had a content of 0%, and therefore, it could be confirmed that high purity silicon oxide thin film was formed (FIG. 8).

In addition, an etch rate of the deposited thin film was confirmed by using buffered oxide etchant (BOE) solution (300:1). The silicon oxide thin film deposited by using 1,3-diisopropyl-2,4-dimethylcyclodisilazane (Example 1) was etched at a rate of 0.58 Å/sec, and the silicon oxide thin film deposited by using 1,3-diisopropyl-4,4-dimethylcyclodisilazane (Example 6) was etched at a rate of 0.59 Å/sec. As a result obtained by thermal treating each sample at 750° C. for 30 minutes and confirming an etch rate, an etch rate of the oxide thin film of 1,3-diisopropyl-2,4-dimethylcyclodisilazane was 0.47 Å/sec and an etch rate of the oxide thin film of 1,3-diisopropyl-4,4-dimethylcyclodisilazane was 0.54 Å/sec, which was confirmed that an etch rate was decreased.

Figure 9:
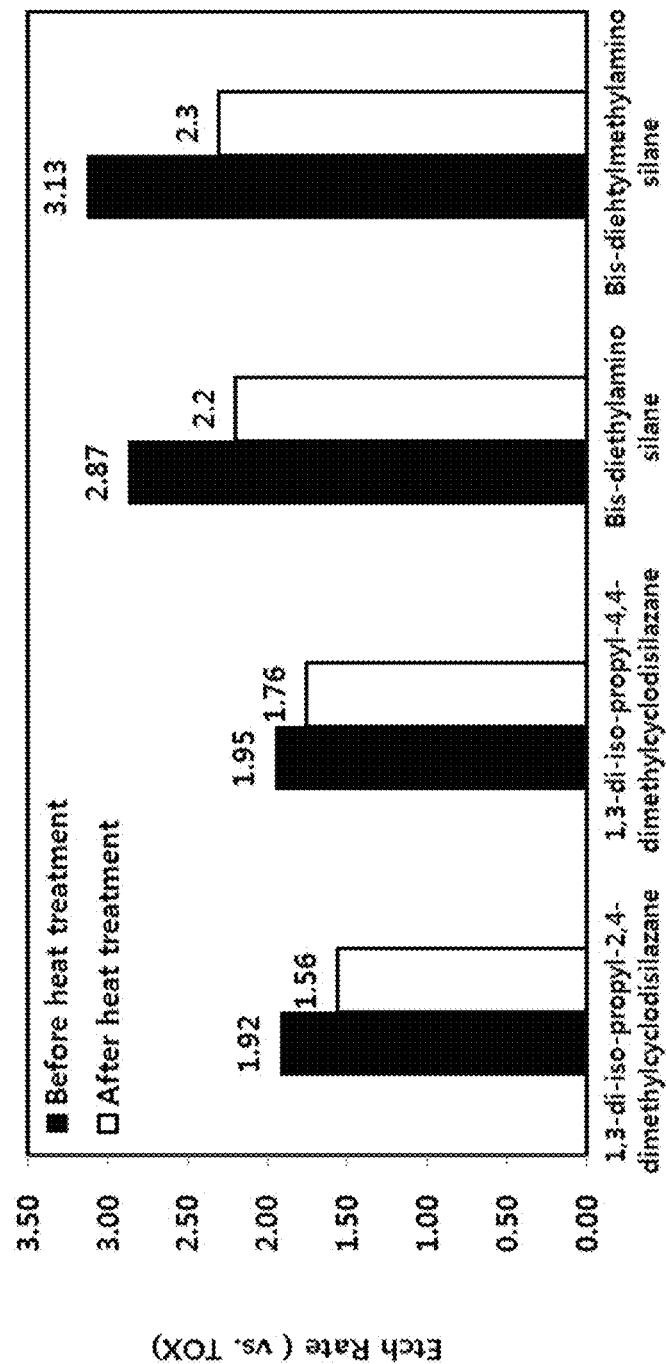
FIG. 9 shows results obtained by an etch rate analysis of the silicon-containing thin films practiced by Example 7 and Comparative Example 1, using an Ellipsometer.

It was confirmed that an etch rate of a thermal oxide thin film deposited at 1000° C. used as a comparative sample was 0.30 Å/sec (FIG. 9).

That is, it was confirmed that the novel cyclodisilazane derivative prepared by the present invention has high utilization value in forming a high purity silicon oxide thin film having a high deposition rate, excellent step coverage, and etch resistance by plasma enhanced atomic layer deposition (PEALD).

COMPARATIVE EXAMPLE 1

Deposition of Silicon Oxide Film by Plasma Enhanced Atomic Layer Deposition (PEALD) Using Known Aminosilyl Amine Compound The film forming evaluation of Comparative Example was conducted by the known PEALD under the same deposition conditions as practiced by Example 7 above except for using known aminosilyl amine compound as shown in the following Table 2, then, the deposited thin film was analyzed by the same analysis method and conditions as practiced by Example 7 above, and the analysis result thereof was obtained. Hereinafter, FIG. 5 and Table 2 specifically show a method for depositing the silicon oxide thin film.

TABLE 2

Silicon Oxide Thin film Deposition Condition

|  | Precursor | |
| --- | --- | --- |
|  | Bis-diethylamino silane (Precursor A) | Bis-ethylmethylamino silane (Precursor B) |
| Heating Temperature (° C.) of Precursor | 40 | 40 |
| Substrate Temperature (° C.) | 100 | 100 |
| Kind of Substrate | Si wafer | Si wafer |
| Injection Time (sec) of Precursor | 0.5 | 0.2 |

TABLE 2-continued

Silicon Oxide Thin film Deposition Condition

| | | Precursor | |
|---|---|---|---|
| | | Bis-diethylamino silane (Precursor A) | Bis-ethylmethylamino silane (Precursor B) |
| Purge | Flow Amount (sccm) | 1100 | 1100 |
| | Time (sec) | 20 | 20 |
| 400 W Oxygen Plasma | Flow Amount (sccm) of Oxygen/Argon | 300/100 | 300/100 |
| | Time (sec) | 10 | 10 |
| Purge | Flow Amount (sccm) | 1100 | 1100 |
| | Time (sec) | 15 | 15 |
| Frequency of Deposition | Cycle | 50 | 50 |

A thickness of each deposited thin film was measured by an Ellipsometer, and formation of $SiO_2$ thin film was analyzed by infrared spectroscopy. In 50 cycles on a Si wafer, the thickness of the thin films were 72.5 Å (precursor A) and 68.5 Å (precursor B), which showed low deposition rate as compared to the cyclodisilazane derivatives practiced by Example 7, and all of the thin films were formed as silicon oxide films (FIG. 7).

In addition, an etch rate of the deposited thin film was confirmed by using buffered oxide etchant (BOE) solution (300:1). The silicon oxide thin film deposited by using precursor A was etched at a rate of 0.86 Å/sec, and the silicon oxide thin film deposited by using precursor B was etched at a rate of 0.94 Å/sec. As a result obtained by thermal treating each sample at 750° C. for 30 minutes and confirming an etch rate, an etch rate of the oxide thin film of the precursor A was 0.66 Å/sec and an etch rate of the oxide thin film of the precursor B was 0.69 Å/sec, which was confirmed that an etch rate was decreased. It was confirmed that an etch rate of a thermal oxide thin film deposited at 1000° C. used as a comparative sample was 0.30 Å/sec (FIG. 9).

EXAMPLE 8

Figure 10:
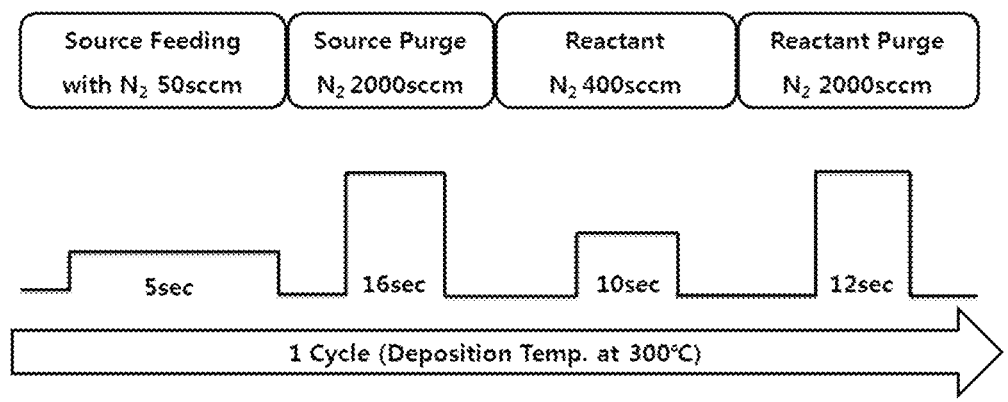
FIG. 10 is a diagram showing a method for depositing a silicon-containing thin film practiced by Example 8.

Deposition of Silicon Nitride Film by Plasma Enhanced Atomic Layer Deposition (PEALD) Using Cyclodisilazane Derivative Film formation evaluation was conducted by using 1,3-diisopropyl-2,4-dimethylcyclodisilazane of Example 1 according to the present invention as a composition for forming a silicon nitride film in a general plasma enhanced atomic layer deposition (PEALD) apparatus using the known PEALD method. Nitrogen together with plasma was used as a reaction gas, and the same nitrogen gas was used for purge. Hereinafter, FIG. 10 and Table 3 specifically show a method for depositing the silicon nitride thin film.

TABLE 3

Silicon Nitride Thin-Film Deposition Conditions

| | | Precursor 1,3-diisopropyl-2,4-dimethylcyclodisilazane (Example 1) |
|---|---|---|
| Heating Temperature (° C.) of Precursor | | 40 |
| Substrate Temperature (° C.) | | 300 |
| Kind of Substrate | | Si wafer |

TABLE 3-continued

Silicon Nitride Thin-Film Deposition Conditions

| | | Precursor 1,3-diisopropyl-2,4-dimethylcyclodisilazane (Example 1) |
|---|---|---|
| Injection Time (sec) of Precursor | | 5 |
| Purge | Flow Amount (sccm) | 2000 |
| | Time (sec) | 16 |
| 100 W Nitrogen Plasma | Flow Amount (sccm) of Nitrogen | 400 |
| | Time (sec) | 10 |
| Purge | Flow Amount (sccm) | 2000 |
| | Time (sec) | 12 |
| Frequency of Deposition | Cycle | 500 |

A thickness of the deposited thin film was measured by an Ellipsometer, and formation of SiN thin film and components of the thin film were analyzed by infrared spectroscopy and auger electron spectroscopy. In 500 cycles on a Si wafer, a thickness of the thin film was 150.70Å.

Figure 11:
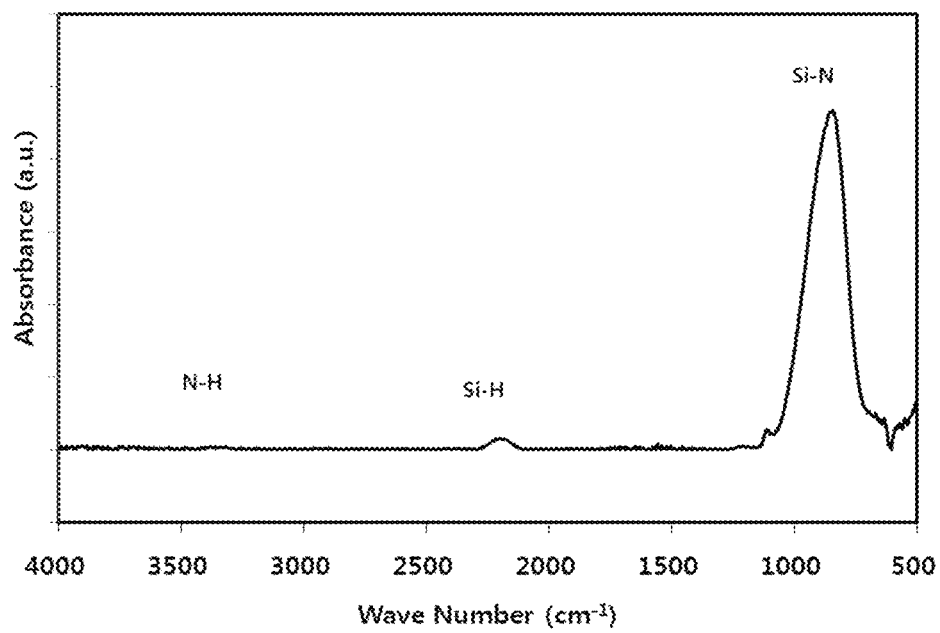
FIG. 11 shows a result obtained by an infrared spectroscopic analysis of the silicon-containing thin film practiced by Example 8.

In addition, as shown in FIG. 11, it was observed that all of the deposited thin films were formed as silicon nitride films, and a small number of bonds such as N—H, Si—H were included.

Further, an etch rate of the deposited thin film was confirmed by using buffered oxide etchant (BOE) solution (300:1). The deposited silicon nitride thin film was etched at a rate of 0.05 Å/sec, and a thermal oxide thin film deposited at 1000° C. used as a comparative sample was etched at a rate of 0.34 Å/sec, and a silicon nitride thin film deposited by low pressure chemical vapor deposition (LPCVD) at 770° C. using dichlorosilane was etched at a rate of 0.02 Å/sec.

That is, it was confirmed that the novel cyclodisilazane derivative prepared by the present invention has high utilization value in forming a high purity silicon nitride thin film having a high deposition rate and excellent etch resistance by plasma enhanced atomic layer deposition (PEALD).

INDUSTRIAL APPLICABILITY

The cyclodisilazane derivative of the present invention has excellent thermal stability and high reactivity, such that the silicon-containing thin film manufacturing by using the cyclodisilazane derivative as a precursor may have high purity and significantly excellent physical and electrical properties.

In addition, the cyclodisilazane derivative of the present invention may have high content of silicon and is present in a liquid state at room temperature and under atmospheric pressure to thereby be easily stored and handled, and may have high volatility and high reactivity to be rapidly and easily deposited, and it is possible to deposit a thin film having excellent cohesion and superior step coverage.

The invention claimed is:

1. A cyclodisilazane derivative represented by the following Chemical Formula 1:

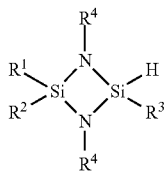

in Chemical Formula 1,
R$^1$ to R$^3$ are each independently hydrogen, halogen, (C1-C5)alkyl or (C2-C5)alkenyl, and
R$^4$ is C3 alkyl or (C2-C5)alkenyl.

2. The cyclodisilazane derivative of claim 1, wherein it is selected from the following compounds:

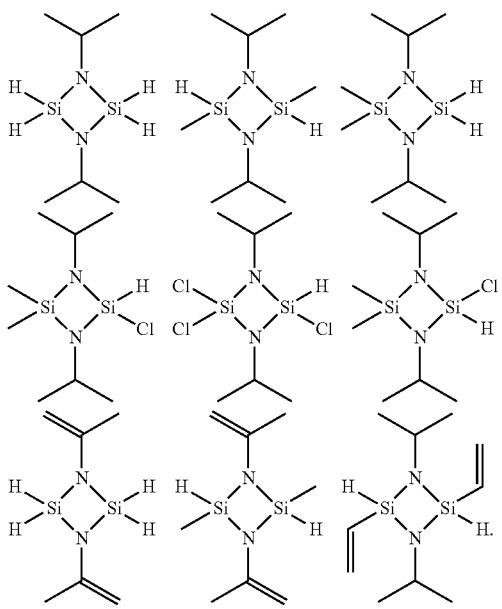

3. A method for preparing a cyclodisilazane derivative represented by the following Chemical Formula 1, comprising:
preparing a diaminosilane derivative represented by the following Chemical Formula 4 by reacting a silane derivative represented by the following Chemical Formula 2 with an amine derivative represented by the following Chemical Formula 3; and
preparing the cyclodisilazane derivative represented by the following Chemical Formula 1 by an intramolecular cyclization reaction of the diaminosilane derivative represented by the following Chemical Formula 4 with a silane derivative represented by the following Chemical Formula 5 in the presence of (C1-C7)alkyllithium:

[Chemical Formula 1]

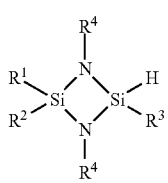

[Chemical Formula 2]

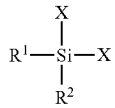

[Chemical Formula 3]

H$_2$N—R$^4$

[Chemical Formula 4]

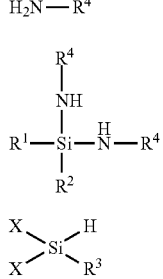

[Chemical Formula 5]

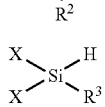

in Chemical Formulas 1 to 5,
R$^1$ to R$^3$ are each independently hydrogen, halogen, (C1-C5)alkyl or (C2-C5)alkenyl, and
R$^4$ is C3 alkyl or (C2-C5)alkenyl, and X is halogen.

4. The method of claim 3, wherein the preparing of the diaminosilane derivative represented by Chemical Formula 4 is performed in the presence of a base represented by the following Chemical Formula 10 or (C1-C7)alkyllithium:

N(R$^6$)(R$^7$)(R$^8$)    [Chemical Formula 10]

in Chemical Formula 10, R$^6$ to R$^8$ are each independently (C1-C7)alkyl.

5. A method for preparing a cyclodisilazane derivative represented by the following Chemical Formula 1-2, the method comprising:
preparing the cyclodisilazane derivative represented by the following Chemical Formula 1-2 by reacting a halocyclodisilazane derivative represented by the following Chemical Formula 1-1 with a metal hydride or an alkali metal derivative represented by the following Chemical Formula 8:

[Chemical Formula 1-2]

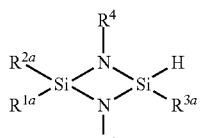

[Chemical Formula 1-1]

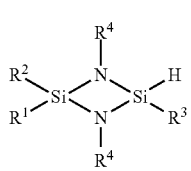

[Chemical Formula 8]

M—R$^{10}$ in Chemical Formulas 1-1, 1-2, and 8,
M is an alkali metal;
R$^{10}$ is each independently hydrogen or (C1-C5)alkyl;
at least one of R$^1$ to R$^3$ is halogen, and the remainder is hydrogen, halogen, (C1-C5)alkyl or (C2-C5)alkenyl;
R$^4$ is C3 alkyl or (C2-C5)alkenyl; and
at least one of R$^{1a}$ to R$^{3a}$ is hydrogen, and the remainder is hydrogen, (C1-C5)alkyl or (C2-C5)alkenyl, wherein when $R^1$ is halogen, $R^{1a}$ is hydrogen, and when $R^2$ is halogen, $R^{2a}$ a is hydrogen, and when $R^3$ is halogen, $R^{3a}$ a is hydrogen.

6. A method for preparing a cyclodisilazane derivative represented by the following Chemical Formula 9, the method comprising:

preparing an aminosilane derivative represented by the following Chemical Formula 6 by reacting a silane derivative represented by the following Chemical Formula 2 with an amine derivative represented by the following Chemical Formula 3;

preparing a halocyclodisilazane derivative represented by the following Chemical Formula 7 by an intramolecular cyclization reaction of the aminosilane derivative represented by the following Chemical Formula 6 in the presence of (C1-C7)alkyllithium; and preparing the cyclodisilazane derivative represented by the following Chemical Formula 9 by reacting the halocyclodisilazane derivative represented by the following Chemical Formula 7 with a metal hydride or an alkali metal derivative represented by the following Chemical Formula 8:

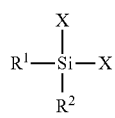

[Chemical Formula 2]

[Chemical Formula 3]

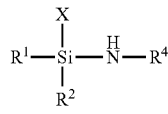

[Chemical Formula 6]

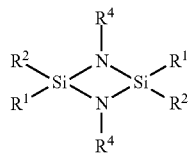

[Chemical Formula 7]

$M\text{—}R^{10}$ [Chemical Formula 8]

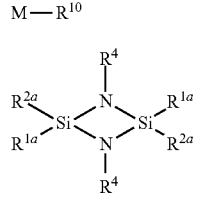

[Chemical Formula 9]

in Chemical Formulas 2, 3 and 6 to 9,
$R^1$ is halogen;
$R^2$ is hydrogen, halogen, (C1-C5)alkyl or (C2-C5)alkenyl;
$R^4$ is C3 alkyl or (C2-C5)alkenyl;
X is halogen;
M is an alkali metal;
$R^{10}$ is hydrogen or (C1-C5)alkyl;
$R^{1a}$ is hydrogen;
wherein when $R^2$ is hydrogen or halogen, $R^{2a}$ a is hydrogen, and
when $R^2$ is (C1-C5)alkyl or (C2-C5)alkenyl, $R^{2a}$ is (C1-C5)alkyl or (C2-C5)alkenyl.

7. The method of claim 6, wherein the preparing of the aminosilane derivative represented by Chemical Formula 6 is performed in the presence of a base represented by the following Chemical Formula 10 or (C1-C7)alkyllithium:

$N(R^6)(R^7)(R^8)$ [Chemical Formula 10]

in Chemical Formula 10, $R^6$ to $R^8$ are each independently (C1-C7)alkyl.

8. The method of claim 6, wherein the metal hydride is one or a mixture of two or more, selected from the group consisting of LiH, NaH, KH and LiAlH$_4$.

9. A composition for depositing a silicon-containing thin film, comprising the cyclodisilazane derivative of claim 1.

10. A method for manufacturing a silicon-containing thin film by using the cyclodisilazane derivative of claim 1.

11. A silicon-containing thin film manufactured by including the cyclodisilazane derivative of claim 1.

12. The method of claim 5, wherein the metal hydride is one or a mixture of two or more, selected from the group consisting of LiH, NaH, KH and LiAlH4.

* * * * *